Figure 1:
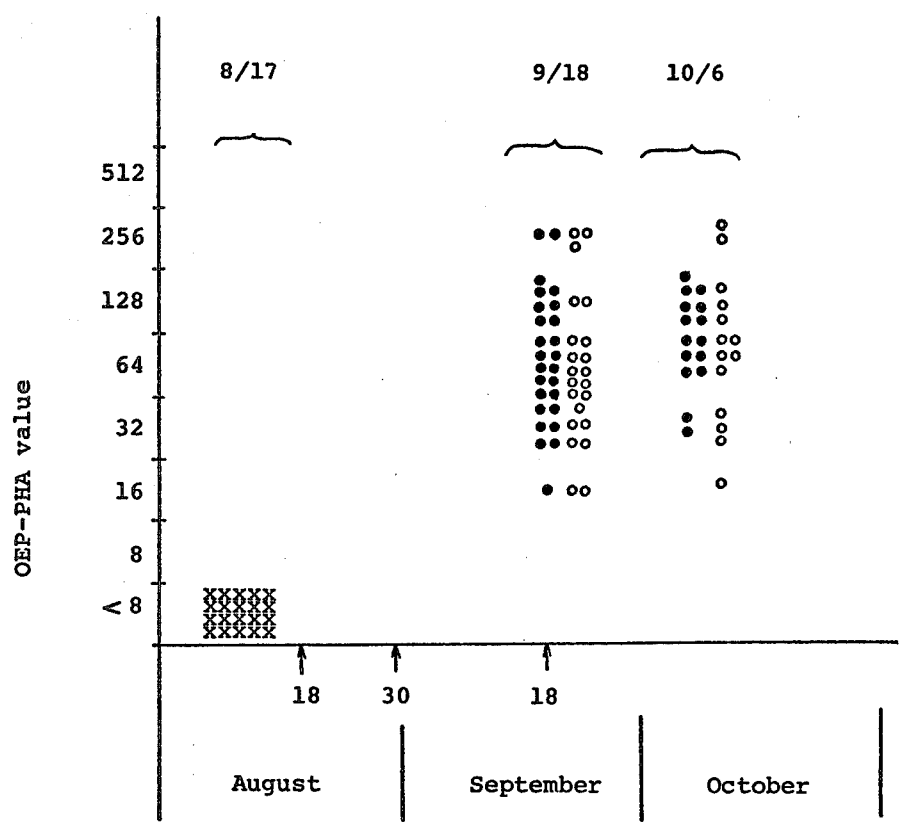

United States Patent [19] [11] 4,157,389
Homma et al. [45] Jun. 5, 1979

[54] MIXED VACCINE AGAINST INFECTIONS BY PSEUDOMONAS AERUGINOSA

[75] Inventors: Yuzuru Homma, Tokyo; Kazuyuki Morihara, Osaka, both of Japan

[73] Assignees: The Kitasato Institute; Shionogi & Co., Ltd., both of Japan

[21] Appl. No.: 763,538

[22] Filed: Jan. 28, 1977

[30] Foreign Application Priority Data

Feb. 5, 1976 [JP] Japan .................................. 51-10838

[51] Int. Cl.$^2$ ...................... A61K 37/48; A61K 39/02
[52] U.S. Cl. ........................................ 424/92; 424/87; 424/94
[58] Field of Search ....................... 424/85, 87, 88, 92, 424/94

[56] References Cited

U.S. PATENT DOCUMENTS

| | | | |
|---|---|---|---|
| 2,528,972 | 11/1950 | Pillemer | 424/92 |
| 3,135,662 | 6/1964 | Pope et al. | 424/92 |
| 3,658,986 | 4/1972 | Tompkins et al. | 424/88 |
| 3,674,863 | 7/1972 | Fisher et al. | 424/92 |
| 3,928,565 | 12/1975 | Homma et al. | 424/92 |
| 3,968,202 | 7/1976 | Stein | 424/92 |
| 3,983,229 | 9/1976 | Relyvbld | 424/92 |
| 3,987,164 | 10/1976 | Homma et al. | 424/92 |
| 4,079,126 | 3/1978 | Homma et al. | 424/92 |

OTHER PUBLICATIONS

Lusis et al., Vet. Bull. 41(3): 169-177, Mar. 1971, "*Pseudomonas aeruginosa*".
Markley and Smallman, J. Bact. 96(4): 867-874, Oct. 1968, "Protection by Vaccination Against Pseudomonas Infection After Thermal Injury".
Jones Journal of Hygeine, (Cambridge), 67:241-247 (1969), "Detoxification of an Immunogenic Fraction from a Culture Filtrate of *Pseudomonas aeruginosa*".
Liu et al., J. Inf. Dis. 128(4): 520-526, Oct. 1973, "Exotoxins of *Pseudomonas aeruginosa* III Characteristics of Antitoxin A".
Pavlovskis et al., Microbiology, pp. 252-256, (1975), "*Pseudomonas aeruginosa* Exotoxin".
Callahan, Infection and Immunity, 14(1): 55-61, (Jul. 1976), "*Pseudomonas aeruginosa* Exotoxin: Purification by Preparative Polyacrylamide Gel Electrophoresis and the Development of a Highly Specific Antitoxin Serum".

*Primary Examiner*—Shep K. Rose
*Attorney, Agent, or Firm*—Wenderoth, Lind & Ponack

[57] ABSTRACT

A three component-mixed vaccine against infections caused by *Pseudomonas aeruginosa* which comprises as the antigens an infection-protective common antigen OEP (Original Endotoxin Protein) obtained from *P. aeruginosa*, an elastase toxoid obtained from *P. aeruginosa* and a protease toxoid obtained from *P. aeruginosa*.

11 Claims, 2 Drawing Figures x  Untreated

●  OEP-PHA value of Group A immunized with OEP

○  OEP-PHA value of Group B immunized with three component-mixed vaccine (OEP + Protease toxoid + Elastase toxoid)

x  OEP-PHA value of Untreated group

●  Protease-PHA value of Group B immunized with three component-mixed vaccine

O  Elastase-PHA value of Group B immunized with three component-mixed vaccine

MIXED VACCINE AGAINST INFECTIONS BY PSEUDOMONAS AERUGINOSA

The present invention relates to a three component-mixed vaccine which comprises as the antigens OEP (Original Endotoxin Protein) obtained from *Pseudomonas aeruginosa*, an elastase toxoid obtained from *P. aeruginosa* and a protease toxoid obtained from *P. aeruginosa*. The three component-mixed vaccine of the invention is useful for prevention and treatment of infections caused by *P. aeruginosa* in human beings and animals.

In both the fields of medicine and veterinary medicine, various important problems caused by *P. aeruginosa* as the typical pathogen in opportunistic infections have been attracting more attention.

Infections caused by *P. aeruginosa*, particularly of serious grade, are apt to occur due to the physiological insufficiency of immunity in newborn infants, the decrease of function of immunity in patients with cancer, leukemia, transplantation and scalding and the depression of immunity due to medication with steroids, imuran and the like.

In the field of veterinary medicine, hemorrahgic pneumonia in minks caused by *P. aeruginosa* and mammitis in bovines caused by *P. aeruginosa* create a serious economic problem in the livestock industry.

Some antibiotics have been recently developed for use against *P. aeruginosa*, but they hardly exhibit an effect due to the insufficiency or decrease of function of immunity in living bodies. Also as to the infections caused by *P. aeruginosa* in the field of veterinary medicine as mentioned above, it is practically impossible and commercially unprofitable in case of minks to treat several thousands to several ten-thousands of animals with antibiotics. The problem of mammitis in bovines exists in almost similar circumstances. Therefore, an immunotherapy in place of the chemotherapy or a combined treatment with them is eagerly awaited.

With regard to immunotherapy, a common antigen OEP protecting against all of the infections caused by *P. aeruginosa*, irrespective of the kind of the strain according to the serotype (13 kinds or more being known at present), has been already isolated and begun to be applied in practical use by Homma et al. (J. Y. Homma et al., Japan. J. Exp. Med., 45, 355–360 (1975); J. Y. Homma et al., Japan. J. Exd. Med., 42, 23–34 (1972); J. Y. Homma, Microbial Drug Resistance, Tokyo University Press, Tokyo, 267–279 (1975); J. Y. Homma, The Fourth International Congress of Animal, Plant and Microbial Toxins, Plenum, London (1975)).

*Pseudomonas aeruginosa* produces protease, elastase and other substances outside the bacterial cell. These two enzymes were proven to act as pathogenic factors (K. Kawaharajo et al., Japan. J. Exp. Med., 45, 79–88 (1975); K. Kawaharajo et al., Japan. J. Exp. Med., 45, 515 (1975); K. Kawaharajo et al., Japan. J. Exp. Med., 44, 435–442 (1974); J. Y. Homma et al., Japan. J. Exp. Med., 45, 89–100 (1975); K. Okada et al., Japan. J. Exp. Med., 46, 245–246 (1976)). This is sufficiently deduced from the fact that high antigen values of protease and elastase are confirmed as well as OEP in sera of patients with chronic *P. aeruginosa* infection in the aspiratory tract and those of bovines with mammitis caused by *P. aeruginosa* (J. Y. Homma, Japan. J. Exp. Med., 45, 361–366 (1975); T. Tomiyama et al., Japan. J. Exp. Med., 43, 185–189 (1973)).

In effect, it is shown by animal experiments that a very small amount of protease or elastase can cause necrosis of skins and corneal ulcers and impart remarkable pathological alterations to internal organs (K. Kawaharajo et al., Japan. J. Exp. Med., 45, 79–88 (1975); K. Kawaharajo et al., Japan. J. Exp. Med., 45, 515 (1975); K. Kawaharajo et al., Japan. J. Exp. Med., 44, 435–442 (1974); K. Kawaharajo et al., Japan. J. Exp. Med., 45, 89–100 (1975)). It is also shown that, when bacteria producing protease and elastase and bacteria not producing these enzymes are inoculated in corneas of mice, the former bacteria cause formation of ulcers, while the latter do not, which reveals an obvious difference in the pathogenic property between these two kinds of bacteria (J. Y. Homma et al., Japan. J. Exp. Med., 45, 515 (1975)). Similarly, in the intestinal lesions, the De test was positive in rabbits inoculated intraintestinally with the protease and elastase producing strain of *P. aeruginosa* whereas it was negative in those inoculated with the no-producing strains.

Therefore, in order to assure a sufficient effect of the immunotherapy, neutralization of the poisonous action by the metabolites is necessary as well as inhibition of bacterial growth by the common infection-protective antigen OEP. For this purpose, the immunization must be effected with toxoids of protease and elastase.

While OEP vaccine is considered as effective for protection against infections caused by *P. aeruginosa*, the extensive study has been made for the purpose of obtaining a more effective vaccine. As the result, it has been found that a three component-mixed vaccine prepared by admixing OEP obtained from *P. aeruginosa* with an elastase toxoid obtained from *P. aeruginosa* and a protease toxoid obtained from *P. aeruginosa* exhibits a remarkable effect for prevention and treatment of infections caused by *P. aeruginosa* in comparison with the simple vaccine comprising OEP alone. This invention based on the above finding.

According to the present invention, there is provided a three component-mixed vaccine which comprises as the antigens an infection-protective common antigen OEP obtained from *P. aeruginosa*, an elastase toxoid obtained from *P. aeruginosa* and a protease toxoid obtained from *P. aeruginosa*.

The infection-protective common antigen OEP used in the present invention is known. Thus, the physical and chemical properties and the preparation process of such OEP are described in the following literature: Japanese Patent Publication (unexamined) No. 40925/1973; J. Y. Homma et al., Japan. J. Exp. Med., 42, 23–34 (1972); J. Y. Homma, Microbial Drug Resistance, Tokyo University Press, 267–279 (1975); J. Y. Homma et al., Abstracts of Lectures at The 22nd Toxoid Symposium, 45–50 (1975).

The elastase toxoid may be prepared from an elastase by its conversion into the toxoid according to a procedure conventionally adopted for production of toxoids of protein toxins, e.g. treatment with formaldehyde or oxymethanesulfinic acid. The starting elastase is known, and its properties and preparation procedure are described in Japanese Patent Publication No. 27315/1965; K. Morihara et al., J. Biol. Chem., 240, 3295–3304 (1965); K. Morihara, J. Bacteriol., 88, 745–757 (1964); K. Morihara et al., Arch. Biochem. Biophys., 123, 572–588 (1968); K. Morihara et al., Agr. Biol. Chem., 39, 1123–1128 (1975).

A typical example for preparation of the elastase toxoid is as follows:

A purified elastase solution (containing 10–15 mg enzyme protein/ml (50 mPU (proteinase unit)/mg enzyme protein), 5 M sodium chloride, 10 mM sodium acetate, 2 mM calcium chloride and 0.1 mM zinc chloride) is diluted with a borate buffer (pH 9) to make an enzyme concentration of 2–5 mg/ml (final concentration of borate being about 0.1 M), and formalin is added thereto to obtain a final concentration of 1% (v/v). The mixture is kept at room temperature. Almost complete deactivation is attained in 1 day. The thus deactivated elastase solution is dialyzed against water and lyophilized to obtain the toxoid.

The term "mPU" hereinabove used is intended to mean a proteinase activity determined by the following procedure:

Casein (2% (v/v); pH 7.4) (1 ml) is admixed with an appropriately diluted solution of the enzyme, and after reaction at 40° C. for 10 minutes, a reaction-stopping solution (containing 0.1 M trichloroacetic acid, 0.2 M acetic acid and 0.2 M sodium acetate) (2 ml) is immediately added thereto. The mixture is kept at the same temperature for 20 minutes to precipitate unreacted casein completely and then filtered. The filtrate (1 ml) is subjected to determination of tyrosine by the Foline's method. By the increase of 1 γ of tyrosine per 1 minute, a proteinase activity of 1 mPU is indicated.

The physical and chemical properties of the thus prepared elastase toxoid are as follows:
1. Molecular weight: 47,000 (gel filtration).
2. Ultraviolet ray absorption spectrum: maximum 278 mμ ($E_{1\%}^{278}$=21.2, 0.1 M KCl), minimum 252 mμ.
3. Isoelectric point: pH 6.5 (electrophoresis with acetate film).
4. Appearance: colorless powder.
5. Composition of amino acid: residues of amino acids (g/100 g protein); aspartic acid (14.2), threonine (5.0), serine (5.6), glutamic acid (6.5), proline (2.9), glycine (5.6), alanine (5.8), valine (4.9), methionine (2.9), isoleucine (2.7), leucine (4.3), tyrosine (9.9), phenylalanine (7.0), lysine (3.9), histidine (2.6), arginine (6.5), cystine/2 (1.2), tryptophane (2.3), ammonia (0.9) (total 94.7 g).
6. Elastase activity: none.
7. Antigen activity: observed.

The protease toxoid may be prepared from a protease by its conversion into the toxoid, for instance, by treatment with formaldehyde or an oxymethanesulfinate in the presence of an amino acid (e.g. lysine). The starting protease is known, and its properties and preparation procedure are described in Japanese Patent Publication No. 27315/1965; K. Morihara et al., Biochem. Biophys. Acta, 73, 113–124, 125–131 (1963); K. Morihara et al., Biochem. Biophys. Acta, 92, 351–360, 361–366 (1964); K. Morihara et al., Arch. Biochem. Biophys., 114, 158–165 (1966); K. Morihara et al., Biochem. Biophys. Acta, 309, 414–429 (1973); K. Morihara et al., Agr. Biol. Chem., 38, (3), 621–626 (1974).

A typical example for preparation of the protease toxoid is as follows:

Crystals of the protease from *P. aeruginosa* (100 mg) are dissolved in a 0.1 M $Na_2HPO_4$ solution containing 0.2 M lysine (about 20 ml), and formalin is added thereto to make a final concentration of about 8% (v/v). The mixture is allowed to stand still at room temperature for 3 days or more and then subjected to dialysis against water and then to lyophilization to obtain the toxoid.

The physical and chemical properties of the thus prepared protease toxoid are as follows:
1. Molecular weight: 63,000 (gel filtration).
2. Ultraviolet ray absorption spectrum: maximum 280 mμ ($E_{1\%}^{280}$=9.27, 0.1 M KCl), Minimum 250 mμ.
3. Isoelectric point: pH 5.2 (focal electrophoresis).
4. Appearance: colorless powder.
5. Composition of amino acid: residues of amino acids (g/100 g protein); aspartic acid (15.6), threonine (5.0), serine (7.6), glutamic acid (9.5), proline (2.1), glycine (7.7), alanine (8.5), valine (5.0), isoleucine (3.9), leucine (8.7), tyrosine (6.9), phenylalanine (5.9), lysine (4.1), histidine (1.9), arginine (2.3), tryptophan (2.3), ammonia (1.4) (total 98.5 g).
6. Protease activity: none.
7. Antigen activity: observed.

For preparation of the three component-mixed vaccine, the infection-protective common antigen OEP, the elastase toxoid and the protease toxoid are dissolved in a solvent in an optional proportion. If necessary, an adjuvant and/or an antiseptic may be added to the resultant solution.

The solvent may be any one suitable for vaccines for human beings and for animals. Specific examples are distilled water, physiological sodium chloride solution, a phosphate-buffered sodium chloride solution, etc.

As the adjuvant, there may be employed any conventional one such as aluminum hydroxide, aluminum phosphate, calcium phosphate, alum or Freund's incomplete adjuvant. The amount of the adjuvant may be appropriately selected from the range of amounts being necessary and sufficient for increasing the immunoactivity. The antiseptic may be also any conventional one such as thimerosal, phenol, carbolic acid or formalin.

The proportion of the components in the three component-mixed vaccine may be optionally changed within the range of effective amounts in order to increase the protective effect as a vaccine for prevention. The effective amount of each component is greatly varied depending on the number of times of immunization and the interval of immunization. It is also varied according to the purpose of the use of the vaccine (i.e. preventive use or therapeutic use).

Some examples of the preferred doses and proportions of the antigens are as follows:

(i) In case of human beings (also in case of bovines):

When immunization is carried out 2 to 3 times per 1 week (without adjuvant), the following proportion is preferred: OEP, 0.1 γ/kg of body weight–10 γ/kg of body weight; protease toxoid, 1 γ/kg of body weight–50 γ/kg of body weight; elastase toxoid, 1 γ/kg of body weight–50 γ/kg of body weight. Depending on the state of immunization, the amounts may be increased appropriately.

(ii) In case of minks:

(a) Preventive vaccine

When immunization is carried out two times (using an adjuvant, the following proportion is preferable: OEP, 10 γ/head–2000 γ/head; protease toxoid, 10 γ/head–2000 γ/head; elastase toxoid, 10 γ/head–2000 γ/head.

When immunization is carried out in one time, the following proportion is recommended: OEP, 500 γ/head–2000 γ/head, protease toxoid, 500 γ/head–4000 γ/head; elastase toxoid, 500 γ/head–4000 γ/head.

(b) Therapeutic vaccine:

When immunization is carried out 2 to 3 times at an interval of 1 week (using or not an adjuvant), the following proportion is favored: OEP, 0.1 γ/head–100 γ/head; protease toxoid, 10 γ/head–2000 γ/head; elastase toxoid, 10 γ/head–2000 γ/head.

The three component-mixed vaccine according to the invention may be administered to animals or human beings through the intramuscular, subcutaneous or intracutaneous route.

The toxicity of each component in the three component-mixed vaccine is as follows:

Toxicity of OEP: intraperitoneal injection to mice with a dose of 100 mg/kg produces temporary asthenia, but the animals do not die.

Pyrexia-inducing property of OEP: by a usual pyrexia test in rabbits, a positive effect is observed with a dose of 0.3 /kg.

In general, the toxicity of OEP as the endotoxin is extremely small in comparison with LPS (lipopolysaccharide) and OEP-LPS complex.

Toxicity of elastase toxoid and protease toxoid: intraperitoneal administration to mice with a dose of 1 mg/mouse does not show any acute toxicity, the minimum lethal dose of protease being 0.2 mg/mouse (i.p.) and that of elastase 0.125 mg/mouse (i.p.).

By immunization with the three component-mixed vaccine of the invention, the effect for protection against infections caused by *P. aeruginosa* is greatly increased, in comparison with the case of immunization with the simple vaccine comprising OEP alone. Therefore, the three component-mixed vaccine is highly useful for prevention and treatment of infections caused by *P. aeruginosa* in animals and human beings.

The antibody or the serum containing the antibody which is obtained by inoculation of the three component-mixed vaccine of the invention to an animal or a human being can be used for protection against lesions of infections caused by *P. aeruginosa* (e.g. corneal ulcer) and for their treatment. This is well proved by corneal ulcers in mice (cf. Experiment 2).

Practical and presently preferred embodiments of the invention are illustratively shown in the following Examples.

EXAMPLE 1

(1) Protease toxoid-potash alum solution: Protease toxoid (100 mg) is dissolved in a phosphate-buffered aqueous sodium chloride solution (M/15, pH 7.4) (PBS) (24.8 ml), and 10% potash alum [$K_2Al_2(SO_4)_4 \cdot 24H_2O$] solution (2.5 ml) is added thereto. To the resultant solution, 20% $Na_2HPO_4 \cdot 12H_2O$ solution (2.5 ml) is further added, and the pH is adjusted to 6.5 to cause complete precipitation. Finally, 1% thimerosal solution (0.3 ml) as the antiseptic is added thereto (1 mg protease toxoid/0.3 ml).

(2) Elastase toxoid-potash alum solution: The preparation is carried out in the same manner as mentioned above but using elastase toxoid in place of protease toxoid.

(3) OEP-potash alum solution: OEP (100 mg) is dissolved in 0.01 N NaOH solution (5 ml), and PBS (28 ml) is added thereto. To the resultant solution, 10% potash alum solution (3.3 ml) and 20% $Na_2HPO_4$ solution (3.3 ml) are added in order, and finally 1% thimerosal solution (0.4 ml) is added (1 mg OEP/0.4 ml).

(4) Immediately before the use, the above prepared protease toxoid-potash alum solution, elastase toxoid-potash alum solution and OEP-potash alum solution are mixed together. In 0.5 ml of this mixed solution, 500 γ of protease toxoid, 500 γ of elastase toxoid and 500 γ of OEP are contained.

EXAMPLE 2

In the same manner as in Example 1 except that 10% aluminum hydroxide solution is used in place of 10% potash alum solution, there are prepared protease toxoid-aluminum hydroxide solution, elastase toxoid-aluminum hydroxide solution and OEP-aluminum hydroxide solution.

Immediately before the use, the above prepared three solutions are mixed together.

It is apparent, from the results of the Experiments mentioned below, that the three component-mixed vaccine according to the invention shows a much higher effect in prevention of infection caused by *P. aeruginosa*, in comparison with the simple vaccine containing OEP alone.

EXPERIMENT 1

PHA (Passive Hemagglutination) value in sera of minks immunized by simple vaccine containing OEP alone or three component-mixed vaccine containing OEP, protease toxoid and elastase toxoid and effect for protection against infection:

(1) Method:

Animals: 5 to 6 month-old female minks (sapphire).

Application of vaccine: subcutaneous or intra-muscular injection.

Challenge test: The strain No. 5 of *P. aeruginosa* which produces both protease and elastase is used. Infection by live bacteria is effected by pouring the bacterial solution (0.5 ml) into the nasal cavity through a vinyl tube under etheral anesthesia.

Determination PHA value: Protease PHA value and elastase PHA value are measured according to the process described in J. Y. Homma et al., Japan. J. Exp. Med., 45, 361–365 (1975). OEP-PHA value is measured according to the process described in T. Tomiyama et al., Japan. J. Exp. Med., 43, 185–189 (1973).

Infection and immunization: Date of immunization, dosage, date of infection and date of autopsy are shown in Table 1

| Animal | Antigen* | Date of immunization | | | Date of challenge | Date of autopsy |
|---|---|---|---|---|---|---|
| | | 8/18 | 8/30 | 9/18 | 10/7 | 10/20 |
| Group A | OEP | 500 γ | 500 γ | 1000 γ | 19th day after final injection for immunization | 13th day after challenge |
| Group B | OEP + Protease toxoid + Elastase toxoid | 500 γ  1000  1000 | 500 γ  500  500 | 1000 γ  1000  1000 | 19th day after final injection for immunization | 13th day after challenge |

Note:
*The simple and three component-mixed vaccines contain 1% potash alum solution as the adjuvant.

(2) Results:

(i) FIG. 1 of the accompanying drawing shows the change of the OEP-PHA value in sera of the minks immunized with the OEP vaccine or the three component-mixed vaccine. In Group A immunized with OEP and Group B immunized with the three component-mixed vaccine, the OEP-PHA values in the sera at the 31st day and at the 49th day after initiation of immunization are almost identical (32–256). No substantial difference is observed between Groups A and B.

Figure 2:
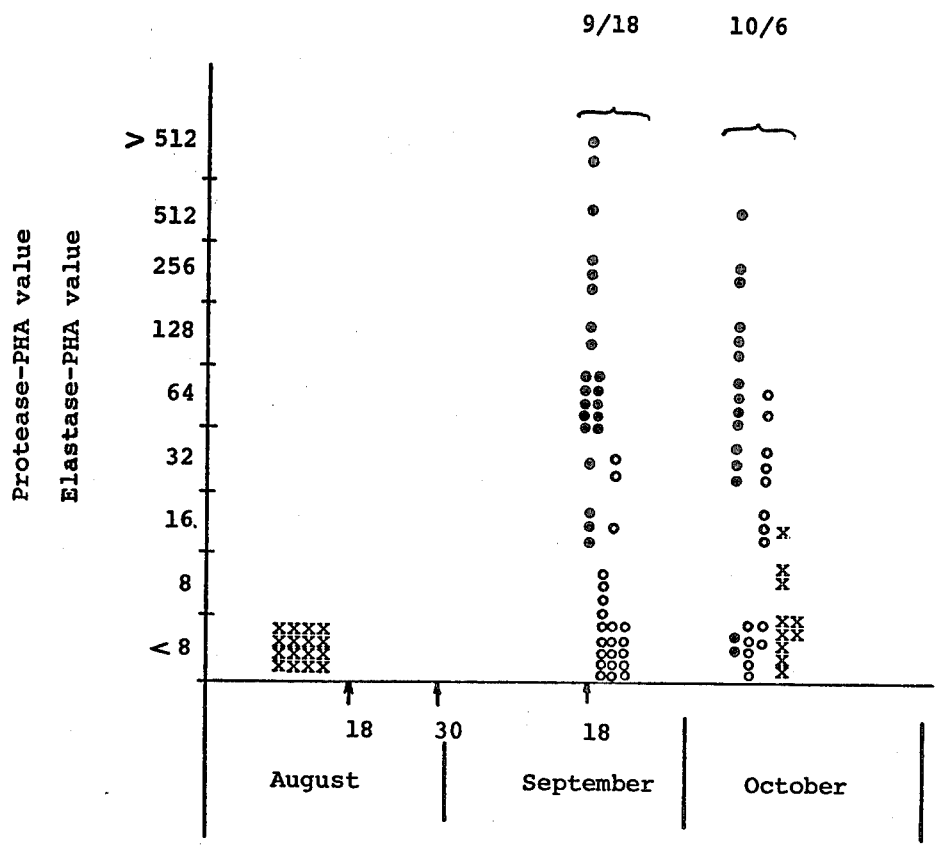

(ii) FIG. 2 shows the protease-PHA value and the elastase-PHA value in sera of the minks immunized with the three component-mixed vaccine. As obvious from FIG. 2, the protease PHA value is well increased and kept at the high level until the day of challenge with live bacteria. The elastase-PHA value is not yet increased at the 31st day after the initiation of the immunization in about two thirds of the minks, but it is somewhat increased at the 49th day in approximately the half of the minks.

(iii) The minks are subjected to live bacteria-infection (challenge test) in order to examine the immunizing effect of the OEP vaccine and the three component-mixed vaccine. The results are shown in Table 2.

Table 2

| Immunizing effect of OEP and three component-mixed vaccine: | | | |
|---|---|---|---|
| Number of bacteria for infection | Untreated group | Group A (treated with OEP) | Group B (treated with OEP + protease toxoid + elastase toxoid) |
| $2 \times 10^5$ | +(2) + (7) | | |
| $6 \times 10^5$ | | +(1) + (1) – – – | – – |
| $2 \times 10^6$ | +(1) + (2) | | |
| $6 \times 10^6$ | | +(2) + (2) – – – | – – – – – |
| $2 \times 10^7$ | +(1) + (4) | | |
| $6 \times 10^7$ | | +(1) + (1) + (1) + (1)– | – – – – – |
| $2 \times 10^8$ | +(1) + (2) | | |
| $6 \times 10^8$ | | +(1) + (1) + (1) + (3)– | +(1) + (1) + (3)– – |
| $2 \times 10^9$ | +(1) + (1) | | |
| $6 \times 10^9$ | | +(1) + (1) + (1) + (2) + (2) | +(1) + (1)– – – – |
| LD$_{50}$ | $3.4 \times 10^{3}$* | $\leq 3.6 \times 10^{6}$** | $>1.9 \times 10^9$ |

Note:
+ means death of one animal.
The parenthesized numeral represents the number of days till the death.
– means survival.
*The numeral represents a value obtained by calculation from the results of several experiments effected in the past (not a result of this experiment).
**A-B $P<0.01$ In case of OEP alone (Group A), the LD$_{50}$ value is $3.6 \times 10^6$ or less. By Group B immunized with the three component-mixed vaccine, to the contrary, the LD$_{50}$ value is larger than $1.9 \times 10^9$ and thus obviously differentiated from Group A. In the untreated group, the LD$_{50}$ value is $3.4 \times 10^3$. In case of immunization with OEP, the LD$_{50}$ value is usually an about 100 to 1000 times amount of live bacteria compared with the untreated group. By the use of the three component-mixed vaccine containing protease toxoid and elastase toxoid in addition to OEP, the immunized animals acquire a resistance against an about $10^4$ to $10^5$ times amount of live bacteria compared with the LD$_{50}$ value of the untreated group.

From the results of this experiment, it is thinkable that the three component-mixed vaccine is an almost ideal vaccine for prevention of infections caused by P. aeruginosa.

EXPERIMENT 2

Treatment of corneal infection in mice with anti-serum and 3',4'-dideoxykanamycin B (DKB):

(i) Method:

Anti-serum: Various anti-serums are obtained by the use of rabbits. The kinds of the anti-serum used and the PHA values are shown in Table 3.

Table 3

| Anti-serum | OEP-PHA | Protease-PHA | Elastase-PHA |
|---|---|---|---|
| OEP serum | 2560 | — | — |
| Protease toxoid serum | 32 | 5120 | 16 |
| Elastase toxoid serum | — | — | 2560 |
| Normal rabit serum | — | — | — |

Infection: A solution containing $10^5$ live bacteria of Pseudomonas aeruginosa (0.01 ml) is dropped to an incised cornea.

Application of anti-serum and DKB:

In case of DKB alone: A DKB solution with varied concentration (800–12.5 γ/0.2 ml) (0.2 ml) is injected intramuscularly to each mouse (6 week-old, female) immediately before infection.

In case of DKB+anti-serum: Anti-serum (0.1 ml) is injected subcutaneously to each mouse 18 hours before the infection. Then, a DKB solution with varied concentration (0.2 ml) is injected intramuscularly immediately before the infection.

For the control group, an aqueous sodium chloride solution is used in place of DKB and anti-serum.

Observation of cornea: The damage of the cornea by the infection is observed for 6 days after the injection. The judgement is made according to the rate of opacity of the cornea and the degree of formation of a gathering and a ulcer.

(ii) Results: Shown in Table 4.

Table 4

Treatment of corneal infection in mice with anti-serum and DKB:

| | | Ratio of efficiency* | | | | |
|---|---|---|---|---|---|---|
| Material injected | ED$_{50}$ of DKB (γ/mouse) | DKB | DKB + normal rabbit serum | DKB + anti-elastase toxoid serum | DKB + anti-protease toxoid serum | DKB + anti-OEP serum |
| DKB + Mixed anti-sera consisting of anti-OEP serum, anti-protease toxoid serum and anti-elastase toxoid serum | 90 | 3.00 | 1.80 | 1.07 | 0.88 | 0.80 |
| DKB + Anti-OEP serum | 175 | 1.71 | 1.31 | 0.64 | 0.45 | |
| DKB + Anti-protease toxoid serum | 185 | 1.69 | 1.00 | 0.60 | | |
| DKB + Anti-elastase toxoid serum | 230 | 1.33 | 0.79 | | | |
| DKB + Normal rabbit serum | 400 | 0.73 | | | | |
| DKB Alone | 620 | | | | | |

Note:
*Figures larger than 1 indicate the positive efficiency.

From Table 4, it is obvious that protease toxoid, elastase toxoid and OEP anti-sera are each more effective than DKB alone. Particularly, the injection of the combination of the three sera shows a notable therapeutic effect.

Still, it was confirmed experimentally that a mixed vaccine comprising an elastase toxoid and a protease toxoid produces a considerable effect against *Pseudomonas aeruginosa*.

What is claimed is:

1. A mixed vaccine against infections caused by *Pseudomonas aeruginosa* which comprises as the antigen, an elastase toxoid obtained from *Pseudomonas aeruginosa* which is formaldehyde or oxymethanesulfinic acid deactivated, and purified by lyophilization and dialysis, said elastase toxoid having the following properties
   (1) molecular weight: 47,000 (gel filtration);
   (2) ultraviolet ray absorption spectrum: maximum 278 mμ ($E_{1\%}^{278}$=21.2, 0.1 M KCl), minimum 252 mμ;
   (3) Isoelectric point: pH 6.5 (electrophoresis with acetate film);
   (4) appearance: colorless powder;
   (5) composition of amino acid: residues of amino acids (g/100 g protein); aspartic acid (14.2), threonine (5.0), serine (5.6), glutamic acid (6.5), proline (2.9), glycine (5.6), alanine (5.8), valine (4.9), methionine (2.9), isoleucine (2.7), leucine (4.3), tyrosine (9.9), phenylalanine (7.0), lysine (3.9), histidine (2.6), arginine (6.5), cystine/2 (1.2), tryptophane (2.3), ammonia (0.9) (total 94.7 g);
   (6) elastase activity: none;
   (7) antigen activity: observed; and a protease toxoid which is also obtained from *Pseudomonas aeruginosa* which has been deactivated with formaldehyde or oxymethanesulfinic acid in the presence of an amino acid, and which is then purified by dialysis and lyophilization said protease toxoid having the following properties:
   (1) molecular weight: 63,000 (gel filtration);
   (2) ultraviolet ray absorption spectrum: maximum 280 mμ ($E_{1\%}^{280}$=9.27, 0.1 M KCl), minimum 250 mμ;
   (3) isoelectric point: pH 5.2 (focal electrophoresis);
   (4) appearance: colorless powder;
   (5) composition of amino acid: residues of amino acids (g/100 g protein); aspartic acid (15.6), threonine (5.0), serine (7.6), glutamic acid (9.5), proline (2.1), glycine (7.7), alanine (8.5), valine (5.0), isoleucine (3.9), leucine (8.7), tyrosine (6.9), phenylalanine (5.9), lysine (4.1), histidine (1.9), arginine (2.3), triptophane (2.3), ammonia (1.4) (total 98.5 g).
   (6) protease activity: none;
   (7) antigen activity: observed.

2. The vaccine according to claim 1 which further comprises an adjuvant.

3. The vaccine according to claim 1 which further comprises an antiseptic.

4. The vaccine according to claim 1 wherein the components are dissolved in a solvent.

5. The vaccine according to claim 1 which further comprises an infection-protective common antigen OEP (original endotoxin protein) obtained from *Pseudomonas aeruginosa*.

6. A method for immunological prevention against or treatment of infection caused by *Pseudomonas aeruginosa* in human beings or animals which comprises administering an effective amount of the vaccine according to claim 5 thereto.

7. The vaccine according to claim 5, which comprises the infection-protective common antigen OEP, the elastase toxoid and the protease toxoid in a proportion of 0.1–10:1–50:1–50.

8. The vaccine according to claim 5, which comprises the infection-protective common antigen OEP, the elastase toxoid and the protease toxoid in a proportion of 10–2,000:10–2,000:10–2,000.

9. The vaccine according to claim 5, which comprises the infection-protective common antigen OEP, the elastase toxoid and the protease toxoid in a proportion of 500–2,000:500–4,000:500–4,000.

10. The vaccine according to claim 5, which comprises the infection-protective common antigen OEP, the elastase toxoid and the protease toxoid in a proportion of 0.1–100:10–2,000:10–2,000.

11. The method according to claim 6, wherein said vaccine is administered to minks.

* * * * *